US00PP24569P3

(12) United States Plant Patent
Caster et al.

(10) Patent No.: US PP24,569 P3
(45) Date of Patent: Jun. 24, 2014

(54) BLUEBERRY PLANT NAMED 'DRISBLUESIX'

(50) Latin Name: ***Vaccinium corymbosum* L.**
Varietal Denomination: DrisBlueSix

(75) Inventors: Brian K. Caster, Salinas, CA (US); Jennifer K. Izzo, Watsonville, CA (US); Arlen Draper, Payson, AZ (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 70 days.

(21) Appl. No.: 13/507,977

(22) Filed: Aug. 10, 2012

(65) Prior Publication Data

US 2014/0047589 P1 Feb. 13, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

*Primary Examiner* — Kent L Bell
(74) *Attorney, Agent, or Firm* — Jondle Plant Sciences Division of Swanson & Bratschun, L.L.C.

(57) ABSTRACT

A new and distinct variety of blueberry plant named 'DrisBlueSix' particularly distinguished by having a very low chilling requirement, very early harvest season with high fruit productivity, and firm, sweet berries with medium acidity, is disclosed.

2 Drawing Sheets

Genus and species: *Vaccinium corymbosum* L.
Variety denomination: 'DrisBlueSix'.

BACKGROUND OF THE NEW PLANT

The invention relates to a new and distinct blueberry variety designated 'DrisBlueSix' and botanically known as *Vaccinium corymbosum* L. This new blueberry variety was discovered in Santa Cruz, Calif. in June 2001 and originated from a cross between the proprietary female parent blueberry plant 'MS122' (unpatented) and the male parent blueberry plant 'FL 92-166 N' (unpatented). The original seedling of the new variety was first asexually propagated at a nursery in Monterey, Calif. via softwood cuttings. 'DrisBlueSix' was subsequently asexually propagated and underwent further testing at a nursery in Santa Cruz, Calif. for twelve years. The present invention has been found to be stable and reproduce true to type through successive asexual propagations via softwood cuttings.

Plant Breeder's Rights for this variety have not been applied for. 'DrisBlueSix' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz, Calif.

1. A very low chilling requirement;
2. Very early harvest season with high fruit productivity; and
3. Firm, sweet berries with medium acidity.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are 11 years old.

DESCRIPTION OF THE NEW CULTIVAR

Figure 1:
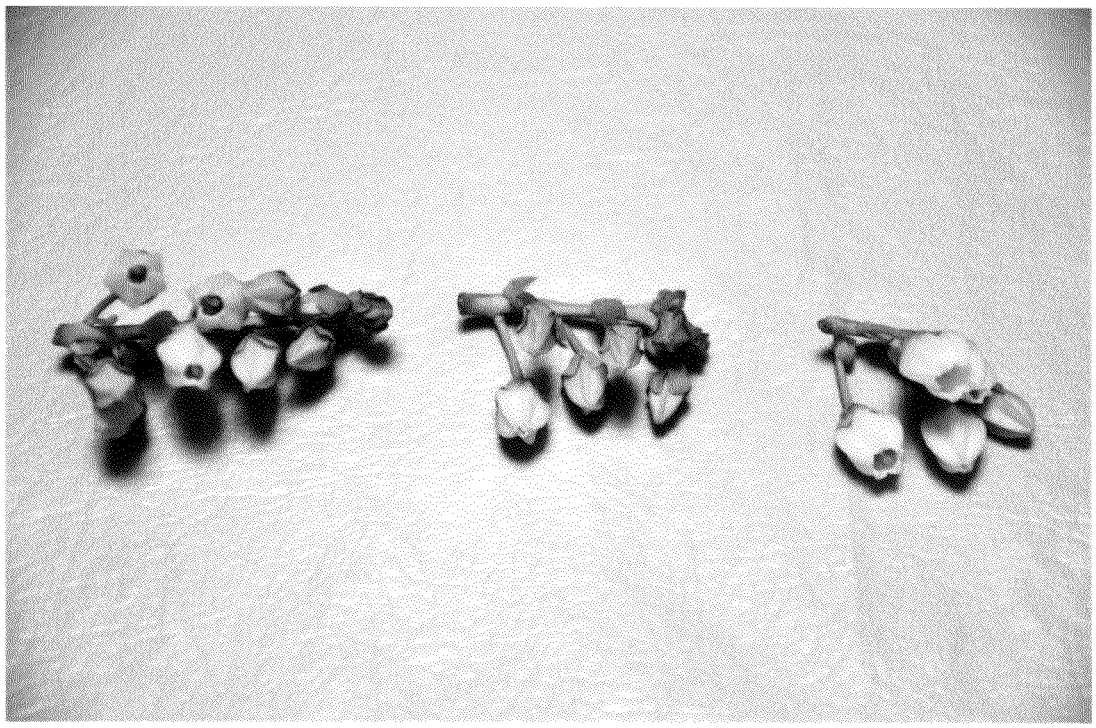
FIG. 1 shows a close-up of the mature flowers.
Figure 2:
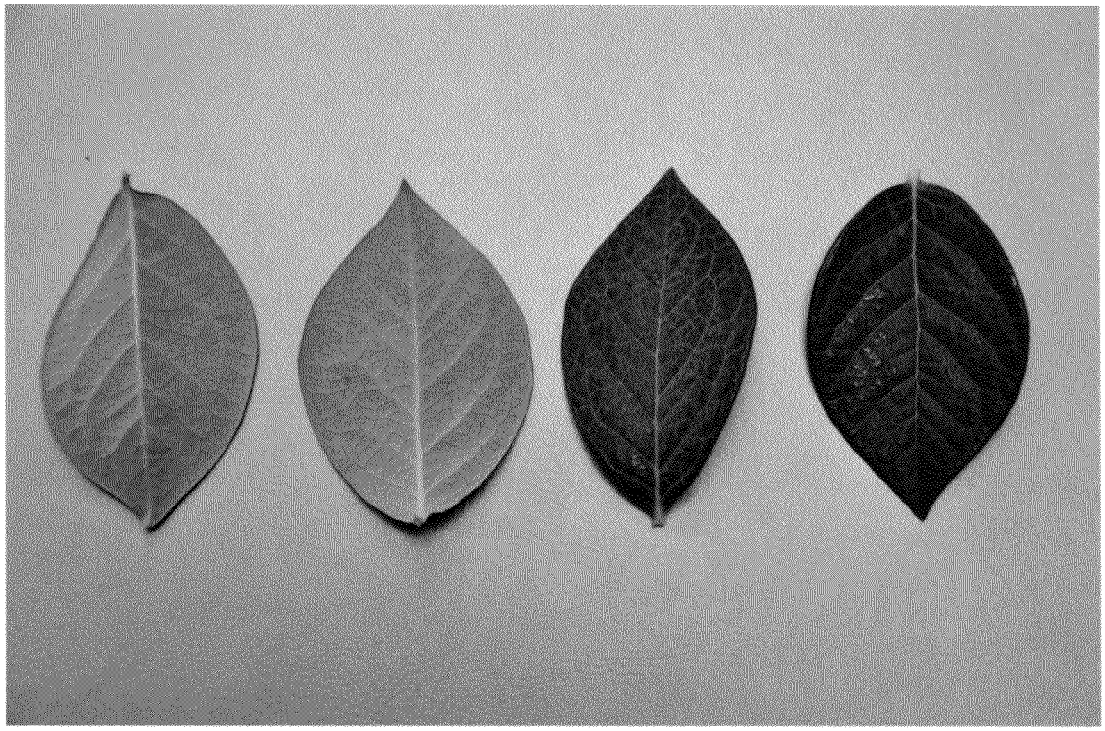
FIG. 2 shows a close-up of the leaves.
Figure 3:
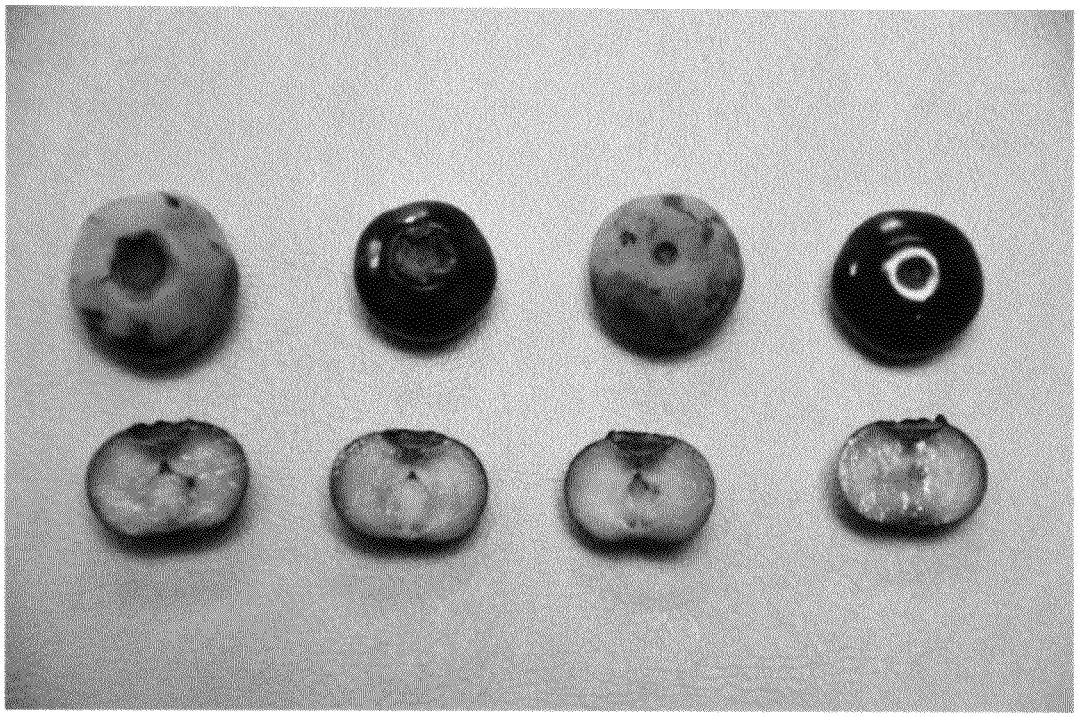
FIG. 3 shows a close-up of the whole fruit, with and without bloom, and a cross-section of the fruit.

The following detailed description sets forth the distinctive characteristics of 'DrisBlueSix.' The data which define these characteristics is based on observations taken in Santa Cruz, Calif. from 2001 to 2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueSix' has not been observed under all possible environmental conditions. The botanical description of 'DrisBlueSix' was taken from 11 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family.*—Ericaceae.
*Botanical.*—*Vaccinium corymbosum* L.
*Common name.*—Blueberry.
*Variety name.*—'DrisBlueSix'.

Parentage:

*Female parent.*—The proprietary blueberry plant 'MS122' (unpatented).

*Male parent*.—The blueberry plant 'FL 92-166 N' (unpatented).

Plant:

*Size*.—Large.
*Height*.—190.5 cm.
*Width*.—169.8 cm.
*Length/width ratio*.—1.1.
*Plant vigor*.—Medium to strong.
*Growth habit*.—Semi-erect.
*Cold hardiness*.—USDA hardiness zone 8B or higher.
*Chilling requirement*.—Very low; 150-250 chilling hours.
*Propagation*.—Soft wood cuttings.
*Time of vegetative bud burst*.—Early.
*Fruiting type*.—Only on one-year-old shoots.
*Cane renewal*.—Strong.
*One-year old canes* (*young canes*).—Length: 109.61 cm. Diameter at the base: 7.06 mm. Diameter at the tip: 3.84 mm. Texture: Smooth. Color (One-year old shoot, branch and canes): RHS 144B (Medium green).
*Five-year old canes* (*mature canes*).—Length: 176.60 cm. Diameter at the base: 21.15 mm. Texture: Rough. Color: RHS 145A (Light yellow-green).

Leaves:

*Length*.—Medium to long; 7.15 cm.
*Width*.—Medium; 4.17 cm.
*Length/width ratio*.—1.7; longer than broad.
*Shape*.—Elliptic.
*Apex*.—Cuspidate.
*Base*.—Cuneate.
*Margin*.—Entire.
*Glossiness*.—Medium to glossy.
*Pubescence*.—Glabrous (Absent).
*Sheath*.—Absent.
*Arrangement*.—Alternate.
*Venation*.—Reticulate.
*Color*.—Upper surface: Dark; RHS N134A (Dark green). Lower surface: Medium; RHS N138C (Medium green).
*Appearance of leaf bud*.—Early to medium.
*Internode length* (*One-year old shoot, upper half*).—Long; 28.76 mm.

Petiole:

*Length*.—5.3 mm.
*Diameter*.—1.36 mm.
*Color*.—RHS 145B (Light yellow-green).

Flowers:

*Length* (*excluding peduncle*).—Medium to long; 9.70 mm.
*Diameter*.—6.51 mm.
*Length/width ratio*.—1.5.
*Petal color*.—RHS 157C (Green-white).
*Flower arrangement*.—Thyrse.
*Flower bud*.—Length: 8.47 mm. Width: 2.80 mm. Color on mature buds: RHS 65C (Light red-purple) and RHS 155B (White). Anthocyanin coloration: Very weak or absent; RHS 63A (Medium red-purple.
*Petal number*.—5 fused petals.
*Petal shape*.—Orbicular.
*Petal apex*.—Lobed.
*Petal margin*.—Fused.
*Petal length*.—9.7 mm.
*Petal width*.—3.69 mm.
*Fragrance*.—Medium.
*Time of beginning flowering on one-year shoot*.—Early.
*Time of flowering* (50% *full bloom*).—Early; March 10.
*Pedicel*.—Length: 9.00 mm. Diameter: 0.67 mm. Color: RHS 144C (Medium yellow-green).
*Corolla*.—Aperture diameter: 3.48 mm. Shape: Urceolate. Size of corolla tube: Small. Corolla tube length: 9.7 mm. Corolla tube diameter: 6.51 mm. Corolla tube color: Very weak or absent; RHS 63B (Medium red-purple). Ridges on tube: Present.
*Peduncle length*.—6.01 cm.
*Peduncle diameter*.—1.9 mm.
*Peduncle color*.—RHS 145A (Medium yellow-green).

Reproductive organs:

*Style length* (*including stigma*).—7.48 mm.
*Ovary color*.—RHS 191B (Medium greyed-green).
*Pollen amount*.—Low to medium.
*Pollen color*.—RHS 4D (Light yellow).
*Anther color*.—RHS N167A (Medium greyed-orange).

Fruit:

*Size*.—Medium to large.
*Length*.—14.60 mm.
*Width*.—19.62 mm.
*Length/width ratio*.—0.7.
*Fruit pedicel diameter*.—1.32 mm.
*Fruit pedicel length*.—9.0 mm.
*Weight*.—3.2 g.
*Number of berries per cluster*.—6.
*Cluster density*.—Medium.
*Shape in longitudinal sections*.—Oblate.
*Intensity of green color* (*immature fruit with bloom*).—Light or clear; RHS 142D (Light green).
*Color of skin* (*mature fruit without bloom*).—RHS 103A (Dark blue).
*Color of skin* (*mature fruit with bloom*).—RHS 98D (Medium violet-blue).
*Intensity of bloom* (*mature fruit*).—Strong.
*Sepals*.—Attitude of sepals: Incurving. Sepal number: 5 fused. Length: 6.2 mm. Width: 4.4 mm fused. Apex: Rounded lobed. Margin: Fused. Color (both inner and outer surfaces): RHS 143C (Medium green).
*Calyx*.—Diameter of basin: Medium; 8.91 mm. Depth of basin: Medium; 4.17 mm. Diameter/depth ratio: 2.1.
*Flesh color*.—RHS 142D (Light green).
*Firmness*.—Firm.
*Sweetness*.—Medium.
*Acidity*.—Medium.
*Time of beginning of fruit ripening* (*one-year old shoots*).—Very early.
*Harvest season*.—Very early.
*Harvest interval*.—May 15 to October 15.

Seeds:

*Length*.—1.69 mm.
*Width*.—1.02 mm.
*Length/width ratio*.—1.7.
*Abundance*.—Low to medium.
*Color*.—RHS 166B (Medium greyed-orange).

Resistance to pests and diseases: Data not available.

COMPARISON WITH PARENTAL AND COMMERCIAL VARIETIES

'DrisBlueSix' differs from parental variety 'FL 92-166 N' (unpatented) in that 'DrisBlueSix' has a very low chilling requirement, whereas 'FL 92-166 N' has a low chilling requirement.

'DrisBlueSix' differs from parental variety 'MS 122' in that 'DrisBlueSix' has a very low chilling requirement, whereas 'MS 122' has a medium chilling requirement.

'DrisBlueSix' differs from the commercial variety 'DrisBlueOne' (U.S. Plant Pat. No. 20,449) in that 'DrisBlueSix' has leaves with a cuspidate apex and firm, oblate shaped berries, whereas 'DrisBlueOne' has leaves with a broadly acute apex and very firm, slightly oblate sphere shaped berries. Additionally, 'DrisBlueSix' has a very low chilling requirement, whereas 'DrisBlueOne' has a medium chilling requirement.

'DrisBlueSix' differs from the commercial variety 'DrisBlueTwo' (U.S. Plant Pat. No. 20,488), in that 'DrisBlueSix' has leaves with an cuneate base and an entire margin, whereas 'DrisBlueTwo' has leaves with a broadly acute base and a serrulate margin. Additionally, 'DrisBlueSix' has oblate shaped berries with a strong bloom intensity on mature fruit, whereas 'DrisBlueTwo' has nearly spherical shaped berries with weak bloom intensity on mature fruit.

We claim:

1. A new and distinct variety of blueberry plant named 'DrisBlueSix' as shown and described herein.

* * * * *